(12) United States Patent
Shi et al.

(10) Patent No.: US 7,479,278 B2
(45) Date of Patent: Jan. 20, 2009

(54) TROPONIN I POLYPEPTIDE FRAGMENTS AND USES THEREOF

(75) Inventors: Qinwei Shi, Etobicoke (CA); Shigui Liu, Mississauga (CA); Mingfu Ling, Toronto (CA)

(73) Assignee: Spectral Diagnostics, Inc, Toronto Ontario (CA)

( * ) Notice: Subject to any disclaimer, the term of this patent is extended or adjusted under 35 U.S.C. 154(b) by 0 days.

(21) Appl. No.: 09/941,997

(22) Filed: Aug. 29, 2001

(65) Prior Publication Data

US 2002/0127602 A1 Sep. 12, 2002

Related U.S. Application Data

(63) Continuation of application No. 09/176,546, filed on Oct. 21, 1998, now abandoned.

(51) Int. Cl.
*A61K 39/00* (2006.01)
*A61K 39/12* (2006.01)
*A61K 39/38* (2006.01)
*A61K 45/00* (2006.01)
*A61K 49/00* (2006.01)

(52) U.S. Cl. ............ 424/185.1; 424/9.2; 424/9.34; 424/184.1; 424/278.1; 424/548; 424/569; 435/68.1; 435/69.1; 435/351; 435/366

(58) Field of Classification Search .......... 424/693, 424/142.1, 548, 569; 435/7.1, 91.4; 530/387.3, 530/388.15; 935/24, 88
See application file for complete search history.

(56) References Cited

U.S. PATENT DOCUMENTS 5,846,738 A 12/1998 Seidel et al.
5,925,533 A 7/1999 Doth et al.
6,077,676 A 6/2000 Shi et al.
6,248,869 B1 6/2001 Morjana et al.
6,268,481 B1 7/2001 Morjana et al.

FOREIGN PATENT DOCUMENTS

| EP | 752426 | 1/1997 |
|---|---|---|
| EP | 780687 | 6/1997 |
| WO | WO94/27156 | 11/1994 |
| WO | WO96/27661 | 9/1996 |
| WO | WO 97/19955 | * 6/1997 |
| WO | WO 97/30085 | * 8/1997 |
| WO | WO 97/39132 | * 10/1997 |
| WO | WO 98/54218 | 12/1998 |
| WO | WO 98/54219 | 12/1998 |

OTHER PUBLICATIONS

Hunkler et al. 1991. Circulation Research. 69:1409-1414.*
Vallin et al. 1990. FEBS. 2701(1,2): 57-61.*
Shi et al. Clinical Chemistry, 45:7 pp. 1018-1025 (1999).

* cited by examiner

*Primary Examiner*—Mark Navarro
*Assistant Examiner*—JaNa Hines
(74) *Attorney, Agent, or Firm*—Klauber & Jackson LLC

(57) ABSTRACT

Polypeptides corresponding to stable, circulating degradation products of troponin I (TnI) are described. The fragments comprise a sequence of the N-terminus of native cardiac TnI with 95-115 amino acid and additionally include fragments lacking about the 20-30 N-terminal amino acids. Utilities of these fragments and antibodies thereto include sensitive detection of myocardial infarction and purification of antibodies sensitive to the detection of troponin I degradation products.

1 Claim, 5 Drawing Sheets

TROPONIN I POLYPEPTIDE FRAGMENTS AND USES THEREOF

CROSS-REFERENCE TO RELATED APPLICATION

This application is a continuation of Ser. No. 09/176,546, filed Oct. 21, 1998, now abandoned, and priority is claimed thereto under 35 U.S.C. 120.

FIELD OF THE INVENTION

This invention relates to new polypeptides corresponding to human cardiac troponin I N-terminal fragments and their uses as immunogens, affinity reagents, and standards for the preparation and calibration of improved immunoassays for troponin I.

BACKGROUND OF THE INVENTION

Early and accurate assessment of suspected acute myocardial infarction is critically dependent on the sensitive and specific detection and quantitation in blood, serum or plasma of released cardiac muscle intracellular components in order to distinguish a potentially lethal event in need of emergency measures from non-life threatening conditions such as angina and non-cardiac chest pain such as dyspepsia. Early electrocardiographic changes are neither adequately specific nor sensitive, and the medical profession has come to rely on serum biochemical markers of cardiac tissue injury for early diagnosis. Initially, the serum markers creatine kinase (CK) and specifically the cardiac CK-MB isoform were used, and subsequently myoglobin was identified as a more sensitive early indicator of cardiac damage. More recently, the cardiac troponin complex and its subunits have come to be preferred as markers of myocardial damage because of their high cardiac specificity. These tests, along with other markers of cardiac muscle damage, provide a high degree of diagnostic accuracy. If performed in the emergency room, an early and accurate diagnosis of myocardial damage offers great advantage to a suspected heart attack victim.

Troponin is a muscle protein integrally involved in the calcium-dependent regulation of muscle contraction. Troponin exists in both cardiac and skeletal muscle as a non-covalently-bound complex of three subunits, the isoforms troponin C, the calcium-binding subunit, troponin I, the inhibitory subunit, and troponin T, which locates the troponin complex on tropomyosin. Diagnostic tests in which the level of troponin subunits or complexes is measured in bodily fluids frequently utilize purified troponin subunits or complexes as antigens for the preparation of antibodies used in the assay procedure, as well as the purified subunits or complex used as controls and calibrators in performing the assays. Assay calibrators are used to prepare a series of dilutions by which a standard curve across the operating range of an assay is generated; assay controls are used to confirm that an assay is operating properly by ensuring that the assayed value of pre-determined samples fall within an acceptable range around their labeled values. In order for the assay to be calibrated properly, the troponin controls and calibrators must be stable and in a form which is immunodetectable by the antibody.

Upon cardiac muscle injury and necrosis, troponin leaks from heart tissue into circulation, where its sensitive detection can help diagnose a heart attack. The amino acid sequence differences between the cardiac and skeletal muscle isoforms of the troponin subunits are exploited in diagnostic tests which specifically measure the cardiac isoform of the troponin subunits and complexes. Skeletal and cardiac troponin I share great sequence homology at the C-terminus but differ substantially at the N-terminus enabling the development of cardiac troponin I-specific immunodetection methods.

Diagnostic tests for cardiac troponin I are available, for example, the troponin I Stratus(R) test from Dade International, Inc., the Opus(R) test from Behring, and the Access(R) test from Beckman. The Stratus(R) troponin I assay utilizes a monoclonal capture and monoclonal detector antibody. The Access (R) troponin I assay also utilizes a monoclonal capture and monoclonal detector antibody, and its calibrator/control is a complex of native cardiac troponin I and troponin C. The Opus(R) troponin I assay utilizes polyclonal antibodies as both capture and detector.

Because of the differences in the methodology and components among the above-mentioned assays, and the calibrators/controls cannot be used interchangeably among assays. For example, the Stratus(R) assay detects an N-terminal region of troponin I; its calibrators/controls, which employ an N-terminal peptide from cardiac troponin I, are not detectable in the Access(R) and Opus(R) assays, as the antibodies in these latter assays are not directed to the same N-terminal peptide portion of troponin I. On the other hand, the Access (R) assay controls, which are detectable in the Access(R) assay with the highest level of sensitivity and cut-off value of all three assays, measure about four times higher in the Opus (R) assay. In contrast, the Opus(R) assay controls are detected poorly by the Stratus(R) assay. Values provided by the controls of one manufacturer's assay can only be used in interpreting assays run on that assay. This presents a major problem for the adoption of a universal standard and inter-laboratory comparisons of data.

Furthermore, troponin I in vivo is not a stable molecule and undergoes degradation by proteolytic enzymes present in the body. Although it is somewhat protected from proteolysis by complex with troponin C, this complex is non-covalent and thus is subject to dissociation, rendering troponin I susceptible to proteolytic attack. The same susceptibility is evident in calibrators and controls, whether derived from natural or recombinant sources.

To overcome some of the aforementioned difficulties with the stability of troponin I, commonly-owned U.S. Pat. No. 6,077,676, incorporated herein by reference, describes the preparation of a single-chain polypeptide comprising troponin I and troponin C, which is more resistant to proteolysis. WO 97/19955 describes a 153 amino acid fragment of troponin I containing the N-terminus, prepared by cyanogen bromide cleavage of native or recombinant troponin I, followed by purification, for use as a calibrator or control for troponin I assay. The fragments appears to be around the same size as a degradation product of troponin I present in the serum of a patient that had a myocardial infarction. This troponin I fragment proved to be readily detectable by the components of the aforementioned STRATUS® troponin I assay, as this assay utilizes monoclonal antibodies which recognize epitopes contained within the claimed fragment.

It is toward the improvement of assays for troponin I by providing methods and reagents for detecting a stable, circulating form of troponin I that the present invention is directed.

SUMMARY OF THE INVENTION

It is a principal object of the present invention to provide isolated polypeptides which are fragments of human cardiac troponin I consisting of the N-terminus and about 95 to about 105 contiguous amino acids. Such sequences correspond to a stable degradation product of the in-vivo proteolysis of native human cardiac troponin I. A preferred polypeptide of the present invention has an amino acid sequence as depicted in SEQ ID NO:2, and is expressed by *E. coli* having the ATCC number 98824. Other stable N-terminal fragments of Troponin I of the present invention corresponding to in-vivo degradation products may also have a small portion of the native N-terminus absent. Such fragments may comprise the N-terminus from about amino acid 20 to 30, extending to about amino acid 95 to 115 of native troponin I.

The polypeptides of the present invention may be prepared by any of a number of means, including peptide synthesis, selective proteolysis of purified troponin I and subsequent purification of the desired fragment, and by recombinant means; recombinant means are preferred. The invention includes both the amino acid sequence of the aforementioned polypeptides corresponding to the troponin I fragments as well as their corresponding DNA sequences, replicable cloning or expression vehicles carrying the sequences, and host cells such as *E. coli* transformed with the vehicles. Modifications of the nucleotide sequence of the troponin I fragment to facilitate expression in bacteria are encompassed in the present invention.

It is a further object of the present invention to provide a method for the preparation of recombinant polypeptides corresponding to troponin I fragments which comprise contiguous sequences of the N-terminal portion of native human cardiac troponin I consisting of about 95 to about 115 amino acids, and those extending from about amino acid 20-30 to about amino acid 95-115 of native cardiac troponin I.

It is another object of the present invention to provide a method of preparing antibodies that recognize the polypeptides of the present invention, as well as a method of purifying anti-troponin antibodies that recognized the polypeptides. Purification may be achieved by the use of an affinity reagent comprising the polypeptides of the invention in order to purify antibodies that will bind to such polypeptides.

It is yet another object of the present invention to provide a method of preparing troponin I calibrators and controls using the polypeptides of the present invention.

It is yet a further object of the present invention to provide an immunoassay for measuring troponin I in bodily fluids wherein the polypeptides of the invention are used as the immunogen in the preparation of monoclonal or polyclonal antibodies to the polypeptide, and any of a number of assay methods are used to detect troponin I.

These and other aspects of the present invention will be better appreciated by reference to the following drawings and Detailed Description.

BRIEF DESCRIPTION OF THE DRAWINGS

FIG. 4 depicts three Western blots of affinity-purified Troponin I after incubation with normal human serum. The antibodies used in each blot are: (A) monoclonal antibody HTI-05 which recognizes cardiac troponin I near the N-terminus; (B) polyclonal goat anti-Peptide-3 which recognizes the portion of troponin I between amino acids 27 and 39; and (C) monoclonal antibody 8I-18 which recognizes the C-terminal region of cTnI. The lanes in each blot are as follows: 1) molecular weight markers (from top to bottom: 203 Kda, 115 Kda, 83.0 Kda, 49.4 Kda, 34.6 Kda, 29.0 Kda, 20.4 Kda and 7.0 Kda respectively); 2) control serum; 3) rcTnI-spiked serum ; 4) rcTn CI complex spiked serum; 5) rcTn CIT complex spiked serum; 6) empty; 7) the purified troponin I fragment of SEQ ID NO:2; and 8) serum spiked with the purified troponin I fragment of SEQ ID NO:2.

DETAILED DESCRIPTION OF THE INVENTION

Circulating cardiac troponin I is an early and specific indicator of suspected acute myocardial infarction. Sensitive and specific detection methods are necessary to quantify the cardiac injury marker soon after a heart attack such that time-critical measures may be administered immediately to benefit the patient. As described above, the troponin complex and, in particular troponin I, are unstable after their release from cardiac tissue. The complex dissociates into the troponin subunits, and the subunits are susceptible to attack by proteolytic enzymes present in circulation. The lifetime of an intact troponin subunit is therefore limited, and in order to reliably test for troponin in circulation to permit the detection of a cardiac event, a test must be sensitive to the form or forms of troponin that is or are present in circulation.

As will be evident in the Examples below, the invention described herein is based upon the identification of circulating, stable human cardiac troponin I fragments comprising an N-terminal sequence of about 95 to 115 amino acids. Degradation also cleaves 20-30 amino acids from the N-terminus, producing a fragment of about 65 to 95 amino acids in length. These fragments represent stable, cardiac-specific markers present in the circulation of individuals after suffering myocardial infarction, and the present invention is directed to the amino acid sequences of the fragments, methods for preparing polypeptides with the amino acid sequence of the fragments, diagnostic reagents useful for measuring these markers, as well as their use as assay calibrators and controls. As used herein, the term polypeptide, marker or fragment used in the singular refers to an amino acid sequence corresponding to the N-terminal portion of human cardiac troponin I extending from the native N-terminus to about 95 to about 115 amino acids and that with the 20-30 N-terminal amino acids absent.

After identification of the sizes and amino acid sequences of the stable, circulating forms of troponin I described herein, their utility for the development of diagnostic reagents for the measurement of troponin I in circulation was evident, as was the utility of the polypeptides themselves for the calibration and control of in vitro diagnostic assays for troponin I. Furthermore, these polypeptides represent potential universal standards for troponin I assays which, if adopted, provide a benchmark for comparing troponin I data from laboratory to laboratory, thus facilitating the international acceptance of normal and abnormal ranges and multi-site studies on the relationship of troponin I levels with outcomes, among other studies.

One means by which the polypeptides corresponding to the troponin I fragments of the present invention may be prepared is by recombinant methods. A recombinant construct is prepared as an expression or cloning vehicle, or plasmid, and introduced into a host cell for expression. Methods for expression of recombinant proteins are known in the art. Once expressed, a single-chain polypeptide may be purified by standard protein purification methods.

Synthetic polypeptides corresponding to the troponin I fragments of the present invention may be prepared using the well known techniques of solid phase, liquid phase, or peptide condensation techniques, or any combination thereof. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile $N^\alpha$-amino protected 9-fluorenylmethoxycarbonyl (Fmoc) amino acids first described by Carpino and Han (1972, J. Org. Chem. 37:3403-3409). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers, such as sold by ABS.

The troponin I fragments of the present invention may also be prepared by targeted degradation of the native purified or recombinantly expressed troponin I molecule, or fragments thereof, using specific enzymatic or chemical degradation, for example proteases with specific peptide cleavage sites and other methods known to break peptide bonds, and combinations of these methods. The desired troponin I fragments may then be purified by peptide or protein purification methods known to the skilled artisan.

One example of a recombinant polypeptide corresponding to a disclosed troponin I fragment was cloned and expressed in E. coli which approximates the structure of a stable marker: an N-terminal fragment of human cardiac troponin I with the native N-terminus and extending 99 amino acids. It has the amino acid sequence SEQ ID NO:2 and a cDNA sequence of SEQ ID NO:1. Modifications in certain nucleotides were made to facilitate expression in the bacterium, without altering the polypeptide sequence. The E. coli strain has been deposited with the American Type Culture Collection, 10801 University Blvd., Manassas Va. 20110-2209, and has been designated ATCC number 98824.

As new markers of cardiac damage, the polypeptides corresponding to the troponin I fragments of the present invention are useful for preparing antibodies for the immunodetection of stable troponin I fragments present in biological samples, preferably patient plasma or serum, for the diagnosis of heart attack. Such antibodies include but are not limited to polyclonal, monoclonal, chimeric, single chain, Fab fragments, and an Fab expression library.

Various procedures known in the art may be used for the production of polyclonal antibodies to the troponin I fragments. For the production of antibody, various host animals can be immunized by injection with the fragments, including but not limited to rabbits, mice, rats, sheep, goats, etc. In one embodiment, a fragment may be used directly as the immunogen or may be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a troponin I fragment of the present invention, any technique that provides for the production of antibody molecules by continuous cell lines in culture may be used. These include but are not limited to the hybridoma technique originally developed by Kohler and Milstein [*Nature* 256:495-497 (1975)], as well as the trioma technique, the human B-cell hybridoma technique [Kozbor et al., *Immunology Today* 4:72 1983): Cote et al., *Proc. Natl. Acad. Sci. U.S.A.* 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals [PCT/US90/02545]. In fact, according to, the invention, techniques developed for the production of "chimeric antibodies" [Morrison et al., *J. Bacteriol.* 159:870 (1984); Neuberger et al., *Nature* 312:604-608 (1984); Takeda et al., *Nature* 314: 452-454 (1985)] by splicing the genes from a mouse antibody molecule specific for a troponin I fragment polypeptide together with genes from a human antibody molecule of appropriate biological activity can be used; such antibodies are within the scope of this invention.

According to the invention, techniques described for the production of single chain antibodies [U.S. Pat. Nos. 5,476, 786 and 5,132,405 to Huston; U.S. Pat. No. 4,946,778] can be adapted to produce troponin I fragment-specific single chain antibodies. An additional embodiment of the invention utilizes the techniques described for the construction of Fab expression libraries [Huse et al., *Science* 246:1275-1281 (1989)] to allow rapid and easy identification of monoclonal Fab fragments with the desired specificity for a troponin I fragment.

In addition to being useful for the screening of polyclonal and monoclonal antibodies raised as described above, the polypeptides of the present invention are also useful for the purification of immunological reagents such as antibodies which are then capable of being used to measure troponin I in bodily fluids from a human patient. For example, polyclonal antibodies raised using authentic troponin I may be expected to contain antibodies that will bind to numerous epitopes on the authentic troponin I molecule. By using a polypeptide of the present invention as an affinity matrix for purifying antibodies from an animal immunized with native troponin I, troponin complex or an impure mixture containing troponin I, only those antibodies recognizing epitopes on the fragment will be isolated. Such antibodies will be preferably used in an immunoassay for troponin I, because for reasons discussed above, the circulating marker is a degradation product of troponin I.

A solid phase support for use in the affinity purification of antibodies of present invention must have reactive groups in order to attach a binding partner. In another embodiment, the solid phase support may be a useful chromatographic support, such as the carbohydrate polymers SEPHAROSE®, SEPHADEX®, and agarose. As used herein, a solid phase support is not limited to a specific type of support. Rather a large number of supports are available and are known to one of ordinary skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLY-HIPE® resin (obtained from Aminotech, Canada), polyamide resin (obtained from Peninsula Laboratories), polystyrene resin grafted with polyethylene glycol (TENTAGEL®, Rapp Polymere, Tubingen, Germany) or polydimethylacrylamide resin (obtained from Milligen/Biosearch, California). Silica based solid phase supports are commercially available (e.g., from Peninsula Laboratories, Inc.; and Applied Biosystems, Inc.).

A further utility of the polypeptides corresponding to troponin I fragments of the present invention is their use as controls and calibrators for assays which specifically measure the fragments of the present invention in biological samples. Assay calibrators are used to prepare a series of dilutions by which a standard curve across the operating range of an assay is prepared; assay controls are used to confirm that an assay is operating properly by ensuring that the assayed value of pre-determined samples fall within an acceptable range around their labeled values. Calibrators and controls may be prepared, for example, at various concentrations in serum or plasma, and stored as a lyophilized powder for reconstitution with water before use.

In addition to the identification by the inventors herein of troponin I fragments that arise from the incubation of troponin I with human serum, the existence of troponin I fragments in circulation in patients is also supported by the finding of highly different values accorded by the Access(R), Opus(R), and Stratus(R) troponin I assays when used to measure the same sequentially-drawn blood samples from a patient undergoing a heart attack. The differences are theoretically attributable due to the differential recognition of the degradation products of troponin I present in circulation by each assay's reagents. For example, the Access(R) assay is the most sensitive to troponin I but gives the lowest troponin values of the three assays. This assay is known to detect epitopes at or near the C-terminus of troponin I; this segment of the troponin I molecule is rapidly susceptible to early attack by proteolytic enzymes and cleavage from the molecule. In addition, stored serum samples show a decline in detectability of troponin I using the Access(R) assay, further evidence that degradation of troponin I in the presence of serum eliminates a C-terminal portion. One of the two polyclonal anti-troponin I antibodies in the Opus(R) assay recognizes a peptide of troponin I near the N-terminus, as this peptide was used as an immunogen used in preparing antibodies for the assay. The higher values of troponin I in circulation detected by the Opus(R) assay indicate that the part of the N-terminal of troponin I persists in circulation as it is readily detectable by this assay. Further evidence presented below indicate degradation of the N-terminal region at about amino acids 20-30.

Furthermore, as it will be seen in the Examples below, repeated measurements on a sample over time using the Stratus(R) assay shows an apparent increase in the level of troponin I with time. As degradation of the troponin I molecule is occurring during this experiment it suggests that troponin I fragments are more readily detected by the antibodies of the Stratus(R) assay than are the intact troponin I molecule.

The antibodies prepared against the polypeptide sequences corresponding to the troponin I fragments of the present invention may be used in an immunoassay to detect troponin I in bodily fluids. As discussed above, epitopes present on the troponin I fragments may be expected to also be present on authentic troponin I as well as intermediate degradation products, and thus antibodies which will bind to the troponin I fragments of the present invention may also bind to authentic troponin I and its degradation products. Therefore, an immunoassay using the antibodies described above, i.e., antibodies raised against the troponin I fragments of the present invention or those raised against authentic troponin I and then affinity-purified using the fragments herein, may be expected to measure not only troponin I fragments in bodily fluids but also full-length troponin I and its intermediate degradation products. Numerous formats for an immunoassay are known to the skilled artisan, such as radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays. Another immunoassay format is a biosensor device, which detects formation of immnunocomplexes proximal to a surface.

An immunoassay for troponin I fragments of the present invention may be in the format of an immunochromatographic assay. Such a device comprises a solid phase means for conducting a liquid. As used herein, the term "solid phase means for conducting a liquid" refers to a solid support that allows migration of a liquid therethrough, e.g., via capillary action. Many immunochromatographic assay means and formats are known in the art, and can be used in the practice of the present invention. Immunochromatographic assays using a membrane as a solid support in a dipstick or flow-through device are well established for use in the clinical laboratory and for alternative, i.e., non-laboratory, site testing. The usual presentation for an immunochromatographic assay device is a membrane (cellulosic or non-cellulosic) enclosed in a plastic holder. The plastic holder keeps the membrane in a suitable configuration in order to ensure the correct functioning of the entire device. There are many variations of the basic structure of assay devices. For example, Litman et al. (U.S. Pat. Nos. 5,156,952 and 5,030,558) describe an assay method and device for determining the presence of a minimum amount of an analyte in a sample. Ullman et al. (U.S. Pat. Nos. 5,137,808 and 4,857,453) describe an device to house an assay membrane that includes self-contained liquid reagents to aid sample flow. Dafforn et al. (U.S. Pat. No. 4,981,768) describes a device with ports for applying sample and extra liquid. Assay devices are also described by Corti et al. (European Patent Application No. 89118378.2). Greenquist et al. (U.S. Pat. No. 4,806,312), Berger et al. (U.S. Pat. No. 5,114,673), Kromer et al. (EP-A 0 229 359), Jackowski (U.S. Pat. No. 5,290,678), Tom et al. (U.S. Pat. No. 4,366,241), Zuk (EP-A 0 143 574), Bernstein (U.S. Pat. No. 4,770,853), May et al. (WO 88/08534), Ching et al. (EP-A 0 299 428)and Valkirs et al. (U.S. Pat. No. 4,632,901), each of which is incorporated herein by reference in its entirety.

In addition to the utilities of antibodies prepared against the troponin I fragments of the present invention, the fragments themselves may be useful in the conduct of immunoassays and other methods used to measure troponin I and fragments in bodily fluids. The fragments may be utilized as positive controls in such assay by, for example, immobilization at the appropriate locus in a strip-format assay, wherein recognition by an antibody will display a positive result.

The present invention also provides for test kits that may be prepared for the measurement of troponin I and its fragments. Generally, such a kit will comprise means for detecting the presence of troponin I in a biological sample from a subject, and means for determining whether this analyte is present at an increased level relative to the level present in a corresponding biological sample from a normal subject, in appropriate containers, and optimally packaged with directions for use of the kit. In one particular aspect, the means for detecting the presence of the marker and for determining whether the marker is present at an increased level comprise a specific binding partner of the marker, such as an antibody as described above, and means for detecting the level of binding of the specific binding partner of the marker to the marker.

The following examples are presented in order to more fully illustrate the preferred embodiments of the invention. They should in no way be construed, however, as limiting the broad scope of the invention.

EXAMPLE 1

Preparation of Recombinant Polypeptides Corresponding to Troponin I Fragments

The cardiac troponin I fragment 1-99 was cloned from the full-length human cardiac troponin I cDNA by polymerase chain reaction using specific primers designed to amplify the TnI 1-99 region. After confirmation by DNA sequencing, the cDNA was then inserted into a pET expression vector. *E. coli* strain BL21(DE3) was transformed with the resulting construct and the selected clones were grown in LB medium for protein production. Modifications of certain codons were made to facilitate expression, without altering the amino acid sequence. TnI 1-99 was isolated from *E. coli* cells using an affinity column coupled with TnI antibodies recognizing the 1-99 region.

The *E. coli* strain was deposited on Jul. 27, 1998, with the American Type Culture Collection. 10801 University Blvd., Manassas, Va. 20110-2209 and accorded Deposit No. 98824.

EXAMPLE 2

Epitope Mapping of Troponin I Fragments

The troponin I fragment described in Example I, as well as a recombinant, full-length troponin I molecule, additionally containing six N-terminal amino acids (as described in U.S. Pat. No. 5,834,210, incorporated herein by reference), were assayed in the STRATUS®, ACCESS®, and OPUS® assays, with the following qualitative results:

|  | Stratus(R) | Access(R) | Opus(R) |
|---|---|---|---|
| SEQ ID NO:2 (N-terminal 99 amino acids) | + | − | + |
| Full-length troponin I plus an additional 6 N-terminal amino acids | + | + | + |

These data demonstrate the differential recognition of the troponin I epitopes by the various assay formats. Each of the assays employ two antibodies, a capture antibody, and a detector antibody. All three assay recognized full-length troponin I. The Stratus(R) and Access(R) assays employ two monoclonal antibodies. The latter recognizes the C-terminal portion of troponin I and thus was unable to detect the fragment of the present invention; the other assay detect the N-terminus and were capable of detecting the fragment.

EXAMPLE 3

A recombinant, full-length troponin I molecule, additionally containing six N-terminal amino acids (as described above) was incubated in 10% human serum for 24 hours at room temperature. Samples were taken at 0, 2, 4, 6, 24, and 48 hours, and the level of troponin I was determined by immunoassay by the Access(R) and the Stratus(R) assavs for troponin I.

Figure 1:
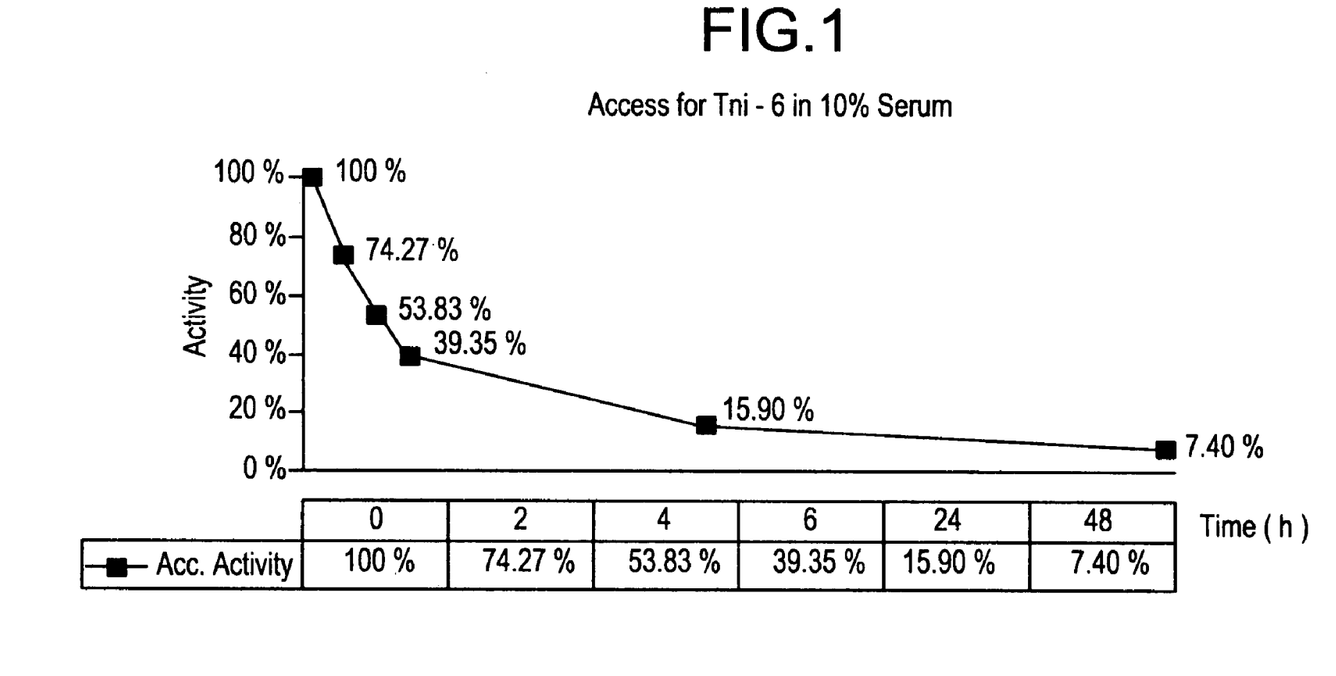
FIG. 1 depicts a graph showing the level of troponin I present in serum over a time course. Troponin I was measured using the Access(R) assay.
Figure 2:
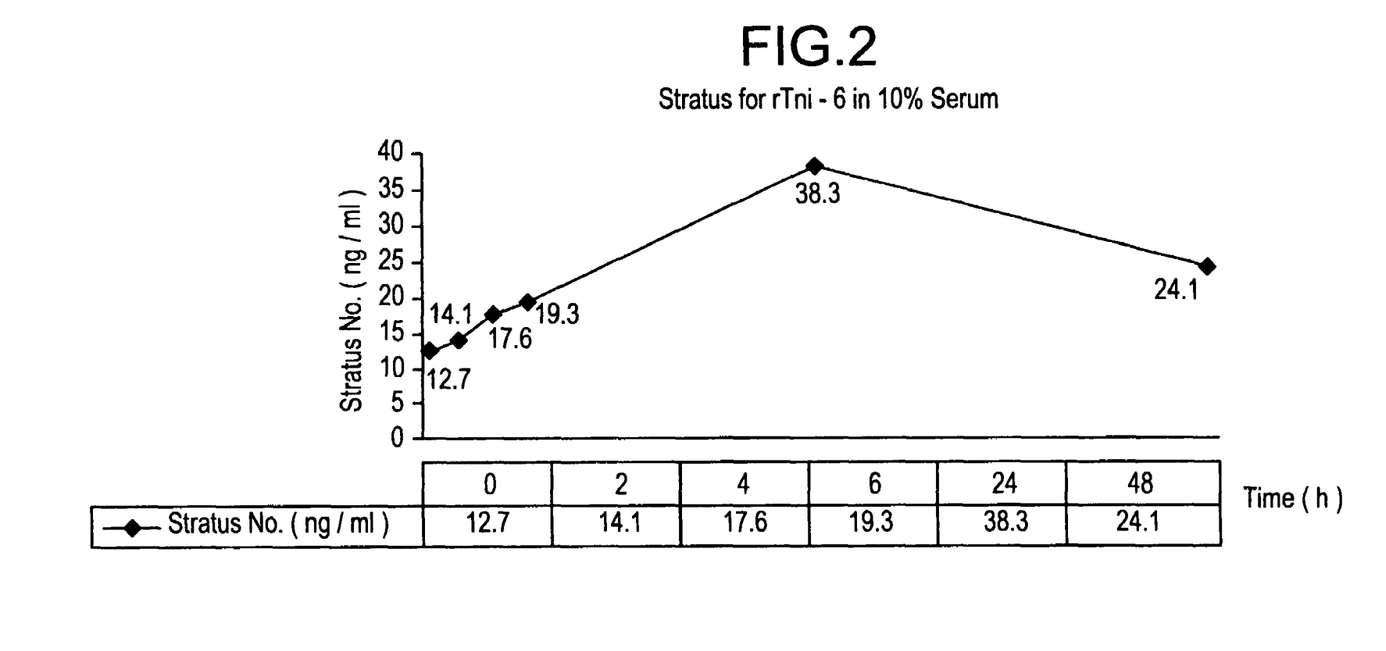
FIG. 2 depicts a graph showing the level of troponin I present in serum over a time course. Troponin I was measured using the Stratus(R) assay.

As shown in FIG. 1, the level of troponin I detected by the Access(R) assay decreased with time, with only 75% of the initial troponin I level present after 2 hours, and only 40% present after 6 hours. At 24 hours, only 16% was present. As described in above, the Access(R) recognizes the C-terminus of troponin I. As shown in FIG. 2. however, when the Stratus (R) assay (which detects a region near the N-terminus) is used on the same samples, an initial increase in detectable troponin I levels is apparent, with an apparent three-fold increase in levels at the 24-hour point, and the level subsequently falling. Thus, it appears that the C-terminus of troponin I is susceptible to early proteolytic attack, followed by the N-terminus.

Figure 3A:
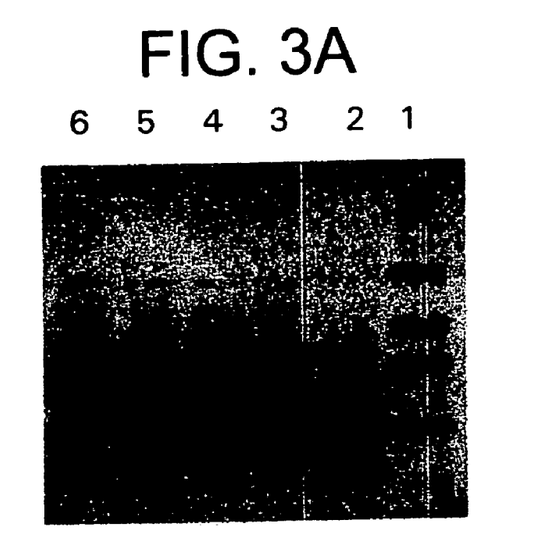
FIG. 3 depicts two Western blots from an electrophoretic gel of a time course of the incubation of troponin I in serum. Gel (A) was stained with a goat polyclonal antibody (anti-Peptide-3) which is directed against amino acids 27 to 39 at the N-terminus of troponin I, gel (B) was stained with an antibody (8I-18) directed against the C-terminus of troponin I.
Figure 3B:
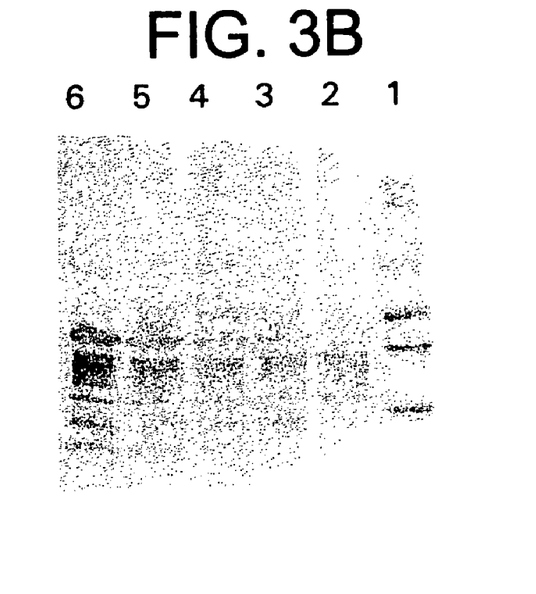

Gel electrophoresis of the samples described above was performed at the same time points, and the troponin I was detected either with an antibody directed against the N-terminal region (FIG. 3A) or the C-terminal region (FIG. 3B) of the troponin I molecule. Lane 1 depicts molecular weight standards, then lanes 2-6 correspond to the 24, 6, 4, 2, and 0 hour time points. As can be seen in FIG. 3A, using an antibody against the N-terminal portion of troponin I, there is a loss of detection of full-length troponin (arrow) over time, with the accumulation of two low molecular weight polypeptides. Using the antibody against the C-terminal peptide, no accumulation of proteolytic fragments was observed.

It is apparent from these results that the troponin I molecule is unstable in serum, but the detectability differs depending on the type of assay used. The Access(R) assay utilizes an antibody known to recognize the C-terminal region of troponin I; as this detection is lost with time on incubation of troponin I in serum, it is postulated that the C-terminal region of troponin I is subject to proteolytic degradation. This is confirmed in the gel stained with an antibody against the C-terminus showing the inability of detecting the two stable degradation products seen in FIG. 3A.

The Stratus(R) assay utilizes an antibody against the N-terminal portion of troponin I. The increase in detectable troponin I activity is attributable to better recognition by the antibody of the troponin I fragment after proteolytic degradation. As is apparent on the gel stained with an antibody against the N-terminal portion of troponin I, there is also loss of authentic troponin I and the appearance of a new band of about 12K Daltons, corresponding to a troponin I fragments still containing the N-terminal epitope recognized by this antibody.

EXAMPLE 4

In a similar experiment to that described in Example 3, recombinant cardiac troponin I (rcTnI), recombinant troponin C-I complex (rcTnCI), recombinant cardiac troponin C-I-T complexes (rcTnCIT), or the fragment of SEQ ID NO:2 were incubated with fresh, normal human serum at 37° C. for 24 hours. In each preparation, equivalent of 0.5 mg recombinant troponin I was incubated with 5 ml of serum. After incubation, the solution was loaded onto a column containing an affinity matrix to which rabbit anti-cTnI antibodies were conjugated. After washing the column, bound materials were eluted by passage of a pH 2.5 buffer therethrough. The eluate was concentrated to 1 ml, and examined by Wester blotting.

Figure 4A:
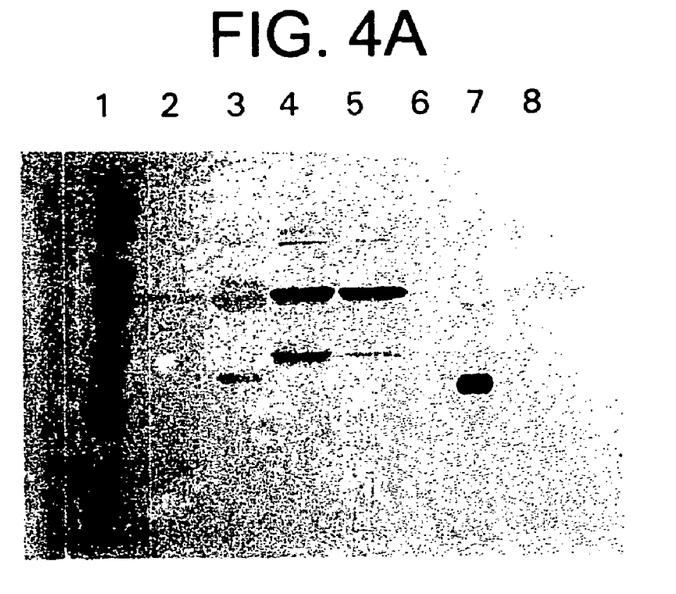
Figure 4B:
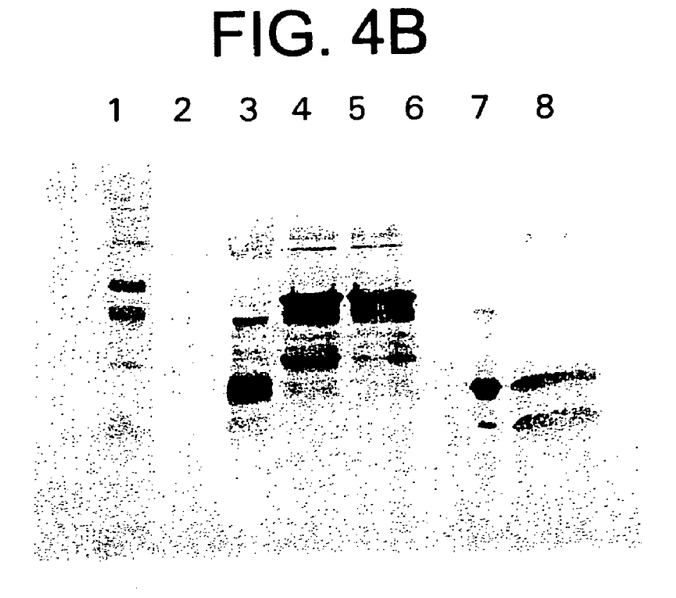
Figure 4C:
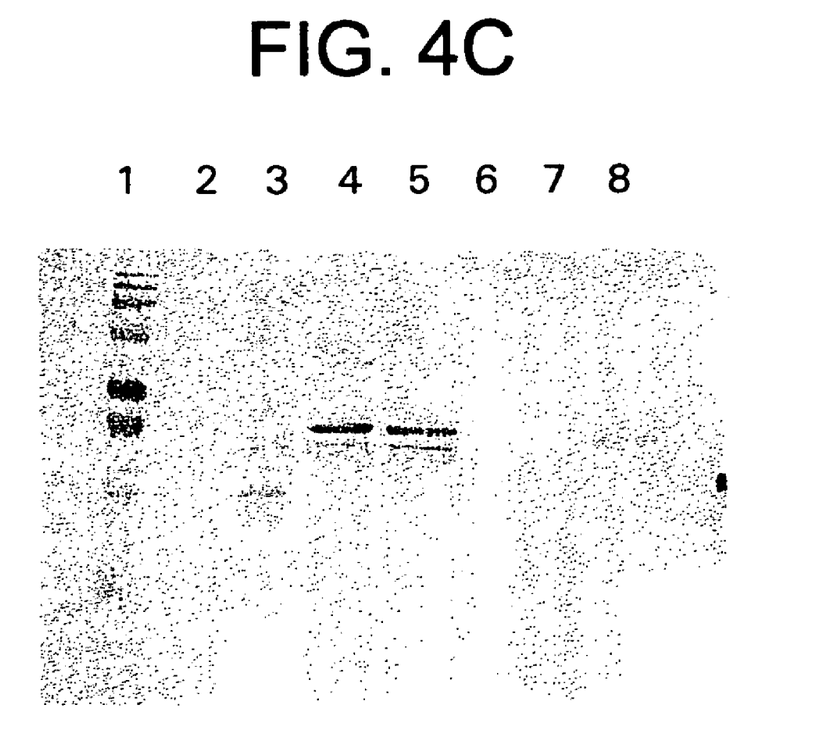

After electrophoresis, gels were incubated with one of the following three antibodies, corresponding to the figures depicting the blots: FIG. 4A) monoclonal antibody HTI-05, which recognizes the near-N-terminus of troponin I; FIG. 4B) polyclonal antibody to Fortron Peptide 3, which recognizes the region about amino acid 27-39 of troponin I; and FIG. 4C) monoclonal antibody 81-18 which recognizes the C-terminal region of TnI. The order of lanes is as follows: Lanes 1) molecular weight markers (from top to bottom: 203 Kda, 115 Kda, 83.0 Kda, 49.4 Kda, 34.6 Kda, 29.0 Kda, 20.4 Kda and 7.0 Kda respectively); 2) control serum; 3) rcTnI-spiked serum; 4) rcTn CI complex spiked serum; 5) from rcTn CIT complex spiked serum; 6) empty; 7) the recombinant troponin I fragment of SEQ ID NO:2; and 8) serum spiked with the recombinant troponin I fragment of SEQ ID NO:2.

Gels A and B show that both monoclonal antibody HTI-05 and polyclonal antibody against Fortron Peptide 3 recognize the purified troponin I fragment of SEQ ID NO:2 (lane 7), which is amino acids 1-99 of native cardiac troponin I. However, after incubation with serum (lane 8), the antibody that recognizes the troponin I region near the N-terminus, HTI-05, fails to recognize the troponin I, but the antibody to amino acids 27-39 still recognizes the troponin I (FIG. 4B, lane 8), which appears in 2 bands. Based on the immunodetectability and the sizes of the fragments, these data indicate that the 1 to 99 amino acid TnI fragment underwent proteolytic degradation, losing about 20-30 amino acids from the N-terminus.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

Various citations to prior publications are mentioned throughout this specification, each of which is incorporated herein by reference in its entirety.

What is claimed is:

1. An isolated polypeptide consisting of SEQ ID NO:2.

* * * * *

SEQUENCE LISTING

```
<160> NUMBER OF SEQ ID NOS: 2

<210> SEQ ID NO 1
<211> LENGTH: 300
<212> TYPE: DNA
<213> ORGANISM: Homo sapiens

<400> SEQUENCE: 1
atggccgatg gttcttctga tgcggctagg gaacctcgcc ctgcaccagc cccaatcaga      60
cgccgctcct ccaactaccg cgcttatgcc acggagccgc acgccaagaa aaaatctaag     120
atctccgcct cgagaaaatt gcagctgaag actctgctgt tgcagattgc aaagcaagag     180
ctggagcgag aggcggagga gcggcgcgga gagaaggggc gcgctctgag cacccgctgc     240
cagccgctgg agttggccgg gctgggcttc gcggagctgc aggacttgtg ccgacagtga     300

<210> SEQ ID NO 2
<211> LENGTH: 99
<212> TYPE: PRT
<213> ORGANISM: Homo sapiens

<400> SEQUENCE: 2

Met Ala Asp Gly Ser Ser Asp Ala Ala Arg Glu Pro Arg Pro Ala Pro
  1               5                  10                  15

Ala Pro Ile Arg Arg Arg Ser Ser Asn Tyr Arg Ala Tyr Ala Thr Glu
             20                  25                  30

Pro His Ala Lys Lys Lys Ser Lys Ile Ser Ala Ser Arg Lys Leu Gln
         35                  40                  45

Leu Lys Thr Leu Leu Leu Gln Ile Ala Lys Gln Glu Leu Glu Arg Glu
     50                  55                  60

Ala Glu Glu Arg Arg Gly Glu Lys Gly Arg Ala Leu Ser Thr Arg Cys
 65                  70                  75                  80

Gln Pro Leu Glu Leu Ala Gly Leu Gly Phe Ala Glu Leu Gln Asp Leu
                 85                  90                  95

Cys Arg Gln
```